United States Patent [19]

Farcot

[11] Patent Number: 5,057,120
[45] Date of Patent: Oct. 15, 1991

[54] APPARATUS FOR THE PERFORMANCE OF AN ANGIOPLASTY OF LONG DURATION

[76] Inventor: Jean-Christian Farcot, 20 Rue Parmentier, 92200 Neuilly, Seine, France

[21] Appl. No.: 291,307
[22] Filed: Dec. 28, 1988

[30] Foreign Application Priority Data

Oct. 27, 1988 [FR] France ................ 88 14022

[51] Int. Cl.$^5$ ............................ A61M 25/10
[52] U.S. Cl. ........................ 606/194; 604/99
[58] Field of Search ............. 600/18; 604/96–104, 604/52, 53, 49, 280–282; 606/192, 194

[56] References Cited

U.S. PATENT DOCUMENTS

| 3,720,199 | 3/1973 | Rishton et al. | 604/98 |
|---|---|---|---|
| 4,154,227 | 5/1979 | Krause et al. | 600/18 |
| 4,299,226 | 11/1981 | Banka | 606/194 |
| 4,456,000 | 6/1984 | Schjeldahl | 604/49 |
| 4,459,977 | 7/1984 | Pizon et al. | 600/48 |
| 4,569,332 | 2/1986 | Schiff et al. | 600/18 |
| 4,581,017 | 4/1986 | Sahota | 604/101 |
| 4,597,755 | 7/1986 | Samson et al. | 604/103 |
| 4,641,654 | 2/1987 | Samson et al. | 606/192 |
| 4,648,384 | 3/1987 | Schmukler | 604/53 |
| 4,655,746 | 4/1987 | Daniels et al. | 604/101 |
| 4,661,094 | 4/1987 | Simpson | 604/53 |
| 4,689,041 | 8/1987 | Corday et al. | 604/49 |
| 4,697,574 | 10/1987 | Karcher et al. | 600/18 |
| 4,748,982 | 6/1988 | Horzewski et al. | 604/102 |
| 4,762,129 | 8/1988 | Bonzel | 604/96 |
| 4,771,777 | 9/1988 | Horzewski et al. | 606/194 |
| 4,771,782 | 9/1988 | Millar | 128/673 |
| 4,808,164 | 2/1989 | Hess | 604/96 |
| 4,838,269 | 6/1989 | Robinson | 606/194 |
| 4,877,031 | 10/1990 | Conway et al. | 604/96 |
| 4,909,252 | 3/1990 | Goldberger | 604/96 |

FOREIGN PATENT DOCUMENTS

| 0192575 | 8/1986 | European Pat. Off. | 600/18 |
|---|---|---|---|
| 0344530 | 12/1989 | European Pat. Off. | 604/96 |

Primary Examiner—C. Fred Rosenbaum
Assistant Examiner—William Lewis
Attorney, Agent, or Firm—Young & Thompson

[57] ABSTRACT

An apparatus for the performance of an angioplasty of long duration comprises a catheter associated with a flexible guide rod and provided with a dilation bulb which is intended to be inflated at the required location. The opposite end of the catheter is connected to a perfusion pump, the operation of which is dependent on a control unit for synchronizing its operation with the electrocardiogram of the patient to be treated in order to carry out downstream of the dilation bulb a perfusion of blood or of oxygen-transporting physiological liquid at a variable flow rate corresponding to the physiological diastole and systole phases of the patient's heartbeat. To this end, the guide rod is mounted on the catheter or on the dilation bulb in order to avoid any interference with the circulation of liquid through the catheter and at the outlet of this latter, thus permitting perfusion of blood or of physiological liquid downstream of the dilation bulb throughout the period of inflation of the bulb.

18 Claims, 3 Drawing Sheets

APPARATUS FOR THE PERFORMANCE OF AN ANGIOPLASTY OF LONG DURATION

BACKGROUND OF THE INVENTION

1. Field of the Invention

The present invention relates to the equipment employed for the performance of an angioplasty in a coronary artery or a peripheral artery.

2. Description of the Prior Art

An operation of this type is at present performed by making use of a catheter fitted on a flexible guide rod and adapted to carry at the distal end a dilation bulb which can be inflated by means of a duct provided for this purpose within the catheter. By means of the guide rod, it is possible to place the inflatable bulb at the precise point at which a dilation is to be carried out for the purpose of flattening atheromatous plates in order to restore a sufficient passage for the flow of blood. However, the disadvantage of this technique lies in the fact that, throughout the period of inflation of the dilation bulb, the blood flow is completely interrupted within the corresponding artery. In the case of a coronary artery, this may cause ischemia of the cardiac muscles, which is liable to give rise to various harmful or dangerous phenomena such as electrical modifications, chest pains, anomalies of left ventricular contractility. Furthermore, this may lead to arythmias which are liable to endanger the life of the patient.

It is for this reason that angioplasties can be performed only during a relatively short period of time of the order of 1 to 3 minutes. Under these conditions, an angioplasty must be repeated several times, thus exposing the patient to the risks mentioned above. Moreover, angioplasties present a restenosis rate of the order of 30% at six months, thus entailing the need to carry out further dilation operations. However, it is apparent from medical publications in this field that the restenosis rate is inversely proportional to the duration of the angioplasty which has been performed.

It is therefore necessary to develop techniques which make it possible to increase the time of inflation of standard dilation bulbs. To this end, it has already been proposed to carry out a perfusion of blood or of an oxygen-transporting physiological liquid downstream of the dilation bulb by employing the catheter itself as a perfusion tube. This makes it necessary to remove the guide rod after positioning of the bulb in order to free the internal space of the catheter. However, this perfusion technique as performed in a continuous mode has not made it possible to obtain fully satisfactory results and extension of the duration of an angioplasty therefore remains very limited.

SUMMARY OF THE INVENTION

The present invention accordingly has for its object an apparatus so designed as to be capable of carrying out a different technique which permits a real extension of the duration of an angioplasty, this being achieved without any attendant danger for the patient to be treated.

To this end, said apparatus is distinguished by the fact that:

on the one hand the distal end of the dilation catheter of standard type is connected to a perfusion pump whose operation is made dependent on a control unit which is capable of ensuring synchronization of its operation with the electrocardiogram of the patient to be treated in order to carry out downstream of the inflated dilation bulb a perfusion of blood or of oxygen-transporting physiological liquid at a variable flow rate corresponding to the diastole and systole phases of the patient's heartbeat, on the other hand the guide rod is mounted on the catheter or on the inflatable bulb carried by this latter so as not to interfere with the circulation of liquid through the catheter and at the outlet of this latter in order to permit perfusion of blood or of physiological liquid downstream of the bulb throughout the period of inflation of this latter.

Under these conditions, the present apparatus makes it possible to carry out downstream of the dilation bulb a controlled perfusion which has a variable flow rate corresponding very precisely to the phases of the heartbeat of the patient who is being treated. In point of fact, experiments performed have served to establish the fact that, in the case of a coronary artery, the disadvantages and risks mentioned earlier can thus be completely avoided since the cardiac muscle is irrigated under conditions close to normal by the blood or by an oxygen-transporting physiological liquid. In consequence, the duration of an angioplasty can be considerably extended with all the advantages which are thus offered.

In an advantageous embodiment of the present apparatus, the unit for controlling the perfusion pump comprises a number of separate and distinct control devices designed to produce operation of said pump in accordance with the particular characteristics of the flow curve, during the diastole and systole phases, which is characteristic of one of the arteries to be treated (such as, for example, anterior interventricular (AIV) artery, circumflex artery, right coronary artery, peripheral arteries), control elements for putting one device or another into service according to requirements, and the arrangement of the control unit being such that the operation of the device which is put into service is made dependent on the patient's electrocardiogram, in regard to the moment of starting of the diastole and systole phases.

Under these conditions, the perfusion carried out by the pump is modified in flow rate and in pressure so as correspond very precisely to the normal conditions of blood circulation within the artery being treated, both in the case of a coronary artery and in the case of a peripheral artery.

In order to permit perfusion of blood or of oxygen-transporting physiological liquid through a passage of maximum cross-section within a catheter of standard type, the guide rod is mounted on or within this latter in such a manner as to ensure that its internal passage is not obstructed. To this end, the catheter employed and its guide rod are designed and associated with each other in a special manner. In the various forms of construction which are provided, the arrangement is such as to avoid an effect of jet of the perfused liquid at the outlet of the terminal orifice of the catheter. With this objective, provision is advantageously made at this end for holes located at intervals on its periphery so as to permit discharge of the perfused liquid around the entire end and in a preferential manner with respect to the discharge through the terminal orifice.

DESCRIPTION OF THE PREFERRED EMBODIMENTS

Figure 1:
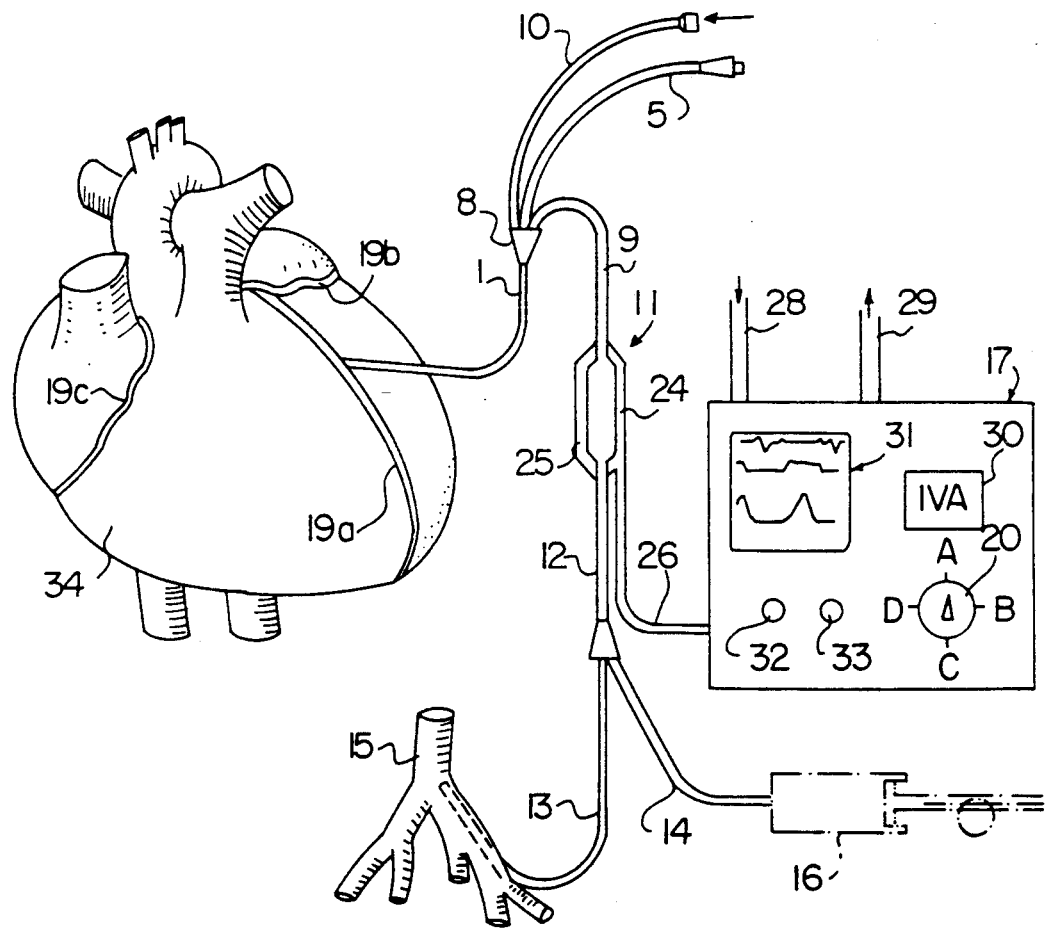
FIG. 1 is a general schematic view illustrating the principle of the apparatus in accordance with the invention, this latter being connected on the one hand to a coronary artery to be dilated and on the other hand to a feed vessel constituted either by a peripheral artery or by a vein belonging to or coming from a highly oxygenated venous system.
Figure 2:
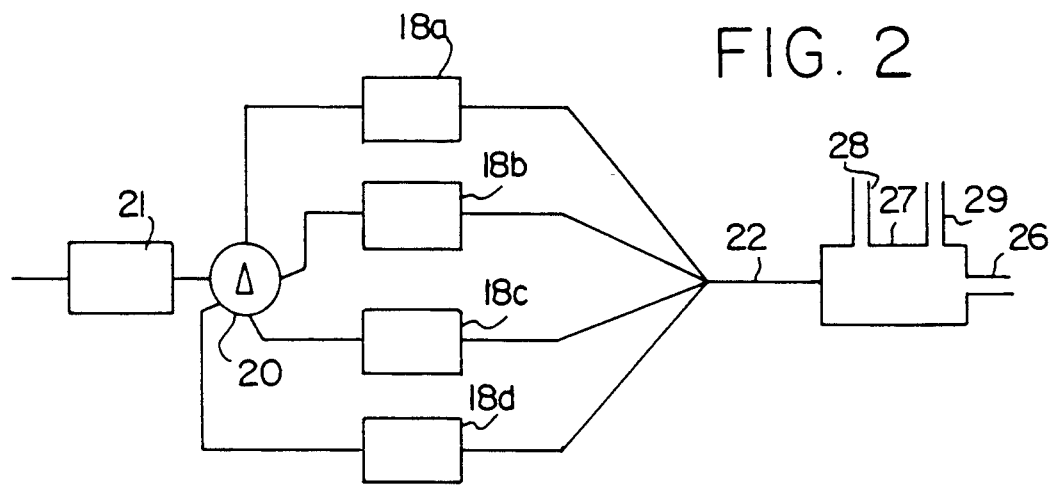
FIG. 2 is a diagram of the circuit of the different control devices provided in this apparatus.
Figure 3:
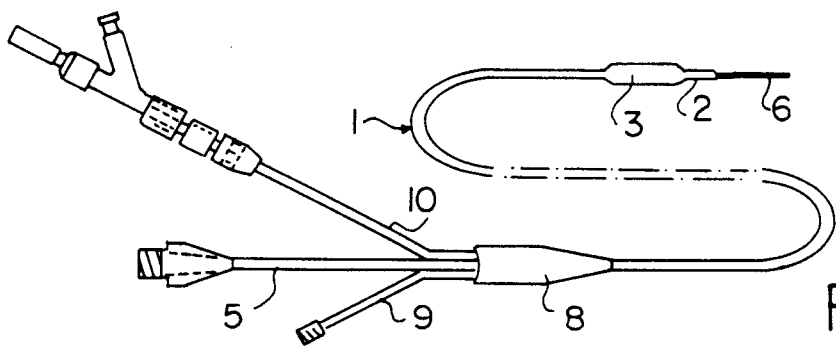
FIG. 3 is a schematic view of the catheter and of its dilation bulb.
Figure 4:
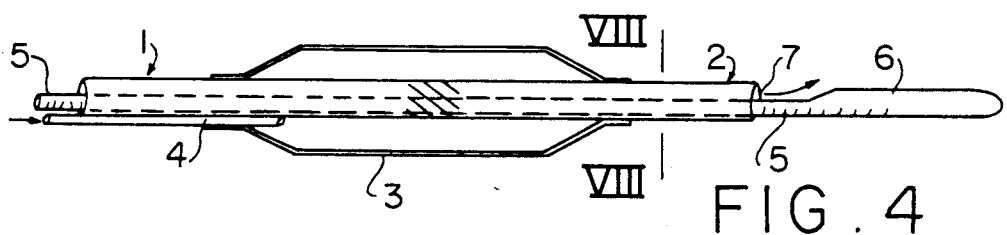
FIGS. 4 to 7 are views in elevation of four different embodiments of the distal end of the catheter.

The apparatus illustrated in FIGS. 1 to 3 comprises a catheter 1, the distal end 2 of which is adapted to carry an inflatable dilation bulb 3. Inflation of said bulb is carried out by means of a separate and distinct tube 4 which is secured to the catheter 1 or incorporated with this latter. The catheter 1 is fitted on a flexible guide rod 5 formed for example by a braided metallic cable or a helically wound wire. In contrast to the catheters employed for angiolasties at the present time, the cross-sectional area of said guide rod 5 is distinctly smaller than that of the catheter and may, for example, be equivalent to one-half or one-third of that of the catheter in order to avoid obstructing the internal space of this latter and to allow a free passageway for the perfusion of blood or of oxygen-carrying physiological liquid on the downstream side of the dilation bulb. However, the end 6 of said guide rod is given an increased cross-section of normal size but distinctly beyond the end 2 of the catheter in order to leave an outlet passage at the location corresponding to the terminal orifice 7 of this latter. It should be noted that this increased cross-section is nevertheless smaller than that of the catheter duct in order to permit sliding displacement of the guide rod within this latter.

The catheter 1 is provided at its opposite end with an end-piece 8 beyond which extends the corresponding end of the guide rod 5. On said end-piece are connected two tubes 9 and 10 which communicate respectively with the catheter 1 and with the tube 4 for inflating the dilation bulb 3.

The tube 9 is intended to convey the perfusion liquid into the catheter 1. To this end, said tube 9 is connected to a pulsatile unit 11 which is intended to serve as a perfusion pump. To the inlet of said pump is connected a feed tube 12 which is subdivided at the upstream end into two pipes 13 and 14. The pipe 13 is constituted by a catheter which can be inserted into a peripheral artery 15 of the patient being treated or else into a vein of a highly oxygenated venous system (inosculation of the renal arteries) of this latter. This pipe 13 is thus capable of supplying the pump 11 with highly oxygenated blood. In regard to the pipe 14, this latter is connected to a force pump 16 which permits injection of a drug or else if so required a supply of oxygen-transporting physiological liquid instead of natural blood.

The pulsatile unit 11 constituting the perfusion pump is capable of drawing the liquid to be perfused from the pipe 13 or 14 and of discharging it periodically towards the tube 9 and the catheter 1. To this end, the operation of said pulsatile unit is made dependent on a control unit designated by the general reference 17. This control unit is so designed that the operation of said perfusion pump is synchronized with the electrocardiogram of the patient being treated in order to ensure that the injection flow of perfusion liquid in the catheter 1 takes place in a variable manner and in synchronism with the diastole and systole phases of the patient's heartbeat.

However, the control unit 17 comprises in addition a number of separate control devices for producing operation of the perfusion pump 11 in accordance with the particular characteristics of the flow curve which is characteristic of any one of the arteries to be treated. Provision can thus be made for four separate control devices indicated by the general references 18a, 18b, 18c and 18d in the diagram of FIG. 2. The first control device 18a corresponds for example to the curve A of flow within the anterior interventricular (AIV) artery 19a, the second control device 18b corresponds to the curve B of flow within the circumflex artery 19b, the third control device 18c corresponds to the curve C of flow within the right coronary artery 19c and finally the last control device 18d corresponds to the curve D of flow within the peripheral arteries.

As shown in the diagram of FIG. 2, a control knob 20 permits the connection of any one of these devices with the general control device 21 which is dependent on the patient's electrocardiogram. In consequence, the control circuit 22 passes through any one of these devices 18a, ... 18d before finally terminating at the system 23 for actuating the perfusion pump.

In the example illustrated, said pump is constituted by a pulsatile unit which may be of the type designed for either pneumatic, hydraulic or electromechanical operation. In the example shown, this pulsatile unit includes a deformable pouch 24 which is placed inside an enclosure 25, said pouch being connected at one end to the feed tube 12 and at the other end to the discharge tube 9. The internal space of the enclosure 25 is connected by means of a tube 26 to the actuating system, namely an electrovalve 27 controlled by the circuit 22. To this electrovalve are connected on the one hand a pipe 28 for the supply of air or liquid under pressure and on the other hand a discharge pipe 29. This makes it possible to control successively the contraction and expansion of the deformable pouch 24 which forms part of the pulsatile unit 11. In consequence, this has the effect of sending a more or less substantial flow of perfusion liquid to the catheter 1 as a function of the orders originating both from the general control device 21 operating in dependence on the patient's heart rate and from any one of the devices 18a, ... 18d corresponding to the inherent characteristics of flow within the artery which is being treated.

In addition to the control knob 20 already mentioned, the casing of the control unit 17 is provided with a screen 30 on which appears an indication for identification of the artery under treatment and corresponding to the position of said knob (for example AVI in the case of the anterior interventricular artery). However, said unit has another screen 31 on which is displayed the electrocardiogram of the patient who is being treated. Finally, the control unit has a turn-on knob 32 as well as one or a number of regulating knobs 33.

The example illustrated in FIG. 1 corresponds to the performance of an angioplasty in the anterior interventricular artery 19a of a patient's heart 34. After introduction of the catheter 1 in this artery and positioning of the dilation bulb 3 in the place at which an angioplasty is to be performed, the control unit 17 is put into operation so as to carry out a perfusion downstream of said bulb throughout the operation. It is clearly necessary to adjust this control unit beforehand as a function of the nature of the artery to be treated. Thus in the example shown, the pointer of the knob 20 is placed opposite to the reference A corresponding to turn-on of the ancillary control device 18a which corresponds to the anterior interventricular artery. In consequence, perfusion downstream of the dilation bulb is performed in accordance with the characteristics of the curve of flow within the corresponding artery and in synchronism with the heart rate of the patient who is treated. In fact, the different ancillary control devices 18a, ... 18d are operated in dependence on the general control device 21 which is in turn dependent on the patient's electrocardiogram. In consequence, the perfusion flow rate is variable and the variations in flow rate correspond to those of the diastole and systole phases, in synchronism with those of the patient's heart rate.

In consequence, irrigation of the heart during angioplasty takes place under conditions identical to or close to normal, thereby avoiding the disadvantages and risks mentioned earlier. For this reason, the duration of the angioplasty can be extended over a long period. This accordingly makes it possible to increase the efficiency of this operation while guarding against any danger of restenosis.

It is worthy of note that the assembly formed by the catheters and other pipes employed with the pump 11 is a system for single use for each patient, this system being intended to be replaced by another after each use of the present apparatus. Furthermore, this system is sterile and the different pipes in which blood is circulated are never in contact with air or with the external atmosphere. Moreover, the apparatus in accordance with the invention is sufficiently powerful to ensure that the pulsatile unit can deliver as much blood or other perfusion liquid as may be necessary to ensure effective physiological perfusion of the zone to be irrigated.

However, the present apparatus can be designed in a number of different alternative embodiments and forms of construction.

Figure 5:
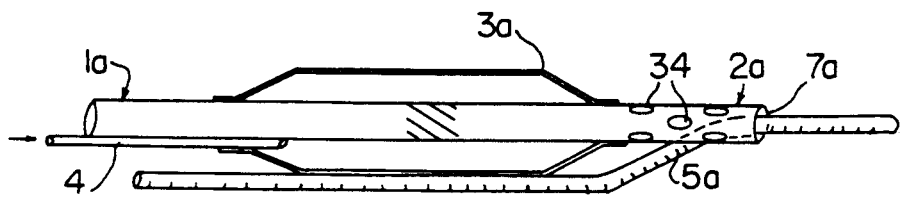

Thus FIG. 5 illustrates another form of construction of the catheter which forms part of the present apparatus. In this embodiment, the flexible guide rod 5a is placed outside the corresponding catheter 1a and outside the dilation bulb 3a carried by this latter. However, the end of said guide rod is engaged in the distal end 2a of the catheter and passes out through the terminal orifice 7a of this latter. Under these conditions, this orifice is almost completely obstructed by said guide rod.

It is for this reason that the end 2a of the catheter is provided with a series of holes 34 which are intended to permit discharge of the perfusion liquid. These holes are accordingly located beyond the dilation bulb 3a but upstream of the point of introduction of the end of the guide rod 5a within the end of the catheter. Under these conditions, the catheter makes it possible to carry out as before a perfusion beyond the dilation bulb throughout the period of inflation of this latter. The existence of holes 34 serves to reduce the force of the jet discharged through the terminal orifice 7a when the guide rod 5a is withdrawn during an angioplasty.

Figure 6:
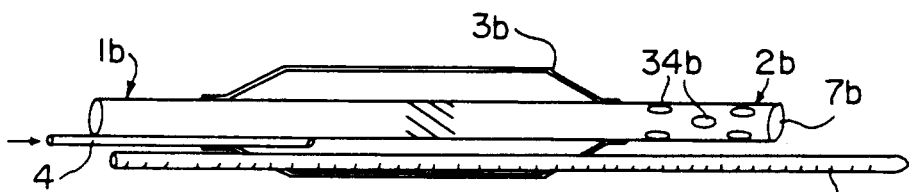

FIG. 6 illustrates another form of construction in which the guide rod 5b is entirely placed outside the corresponding catheter 1b. However, this guide rod is passed through the dilation bulb 3b carried by the catheter. This accordingly provides the desired connection of said guide rod with said catheter.

As in the embodiment shown in FIG. 5, the end 2b of the catheter 1b has a series of holes 34b which are distributed around its periphery and which are intended to permit discharge of the perfusion liquid. In the present case, this discharge can also take place through the terminal orifice 7b of the catheter. However, the peripheral holes 34b are intended to prevent a jet effect at the outlet of the orifice 7b. It is in fact necessary to avoid a jet effect since this would have the disadvantage of detaching or mutilating the endothelium of the vessel which is being treated. To this end, the sum of the cross-sectional areas of the holes 34b is greater than the cross-sectional area of the terminal orifice 7b of the catheter 1b. There is thus a preferential discharge of perfusion liquid through the holes 34b provided at the periphery of the end portion of the catheter.

Figure 7:
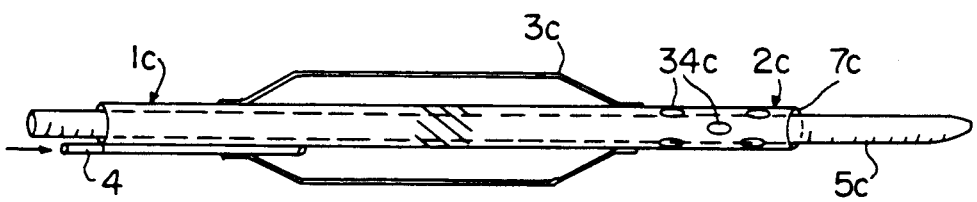
Figure 8:
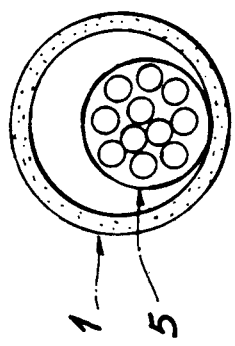
FIG. 8 is a sectional view taken along line VIII—VIII of FIG. 7.
Figure 9:
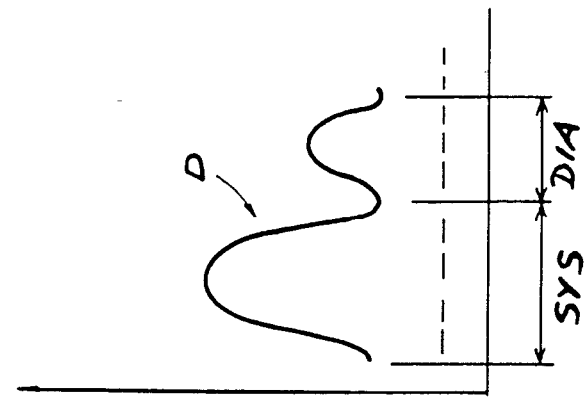
FIGS. 9 to 12 represent the characteristic curves of the blood flow within different arteries which may be treated with the present apparatus.
Figure 10:
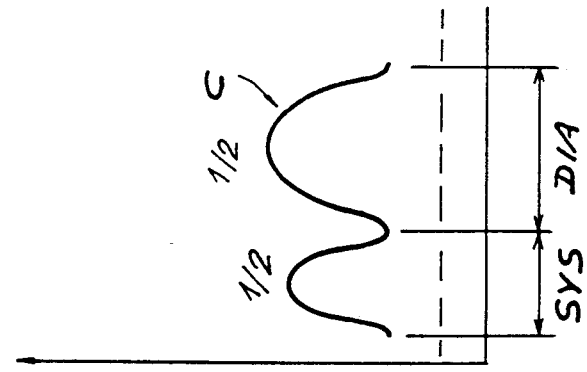
Figure 11:
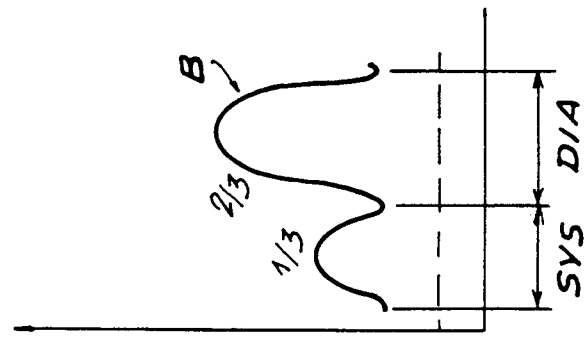
Figure 12:
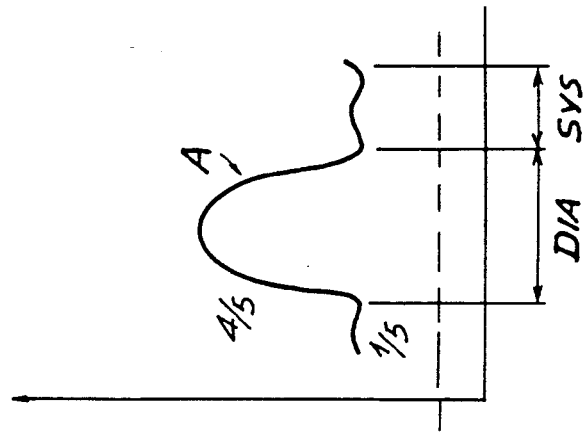

FIG. 7 illustrates yet another embodiment in which the guide rod 5c is intended to be withdrawn from the catheter 1c after positioning of the dilation bulb 3c at the required location. In this form of construction, the distal end 2c of the catheter is provided, as in the case of FIG. 6, with a series of discharge holes 34c formed at its periphery. In this case also, the sum of the cross-sectional areas of these different holes is greater than the cross-sectional area of the terminal orifice 7c of the catheter so as to prevent a jet effect during perfusion after withdrawal of the flexible guide rod 5c.

However, consideration has been given in the foregoing only to examples of construction since the apparatus in accordance with the invention can give rise to many other forms of construction.

What is claimed is:

1. Apparatus for the performance of a long-duration angioplasty of a coronary artery or of a peripheral artery, comprising a catheter having a flexible guide rod and a dilation bulb which is located at a distal end of said catheter and is intended to be inflated at the required location, further comprising:

a perfusion pump connected at a proximate end of the catheter, and a control unit connected to said pump and which is capable of ensuring synchronization of the operation of said pump with the electrocardiogram of the patient to be treated in order to carry out distally of the dilation bulb a perfusion of blood or of oxygen-transporting physiological liquid at a variable flow rate and pressure corresponding to the physiological diastole and systole phases of the patient's heartbeat, and wherein said guide rod extends along said catheter so as not to interfere with the circulation of liquid through the catheter and at the outlet of said catheter, and wherein said guide rod and said catheter are so dimensioned as to permit substantially free perfusion of blood through said catheter, in order to permit perfusion of blood or of physiological liquid distally of the dilation bulb throughout the period of inflation of said bulb;

said apparatus further comprising a tube extending into the inflatable bulb for inflating said bulb, said tube being secured to said catheter and having a substantially smaller diameter than said catheter.

2. Apparatus according to claim 1, wherein the unit for controlling the perfusion pump comprises a number of separate control devices designed to produce operation of said pump in accordance with the particular characteristics of the flow curve, during the diastole and systole phases, which is characteristic of one of the arteries to be treated (for example, anterior interventricular (AIV) artery, circumflex artery, right coronary artery, peripheral arteries), a control element for putting one device or another into service according to requirements, and the arrangement of the control unit being such that the operation of the device which is put into service is made dependent on the patient's electrocardiogram, in regard to the moment of starting of the diastole and systole phases.

3. Apparatus according to claim 1 wherein the guide rod is positioned within the catheter and is adapted to be withdrawn from the catheter after positioning of the dilation bulb at the required location, and the distal end of said catheter is provided with a plurality of discharge holes on its periphery in order to prevent any jet effect of blood or of another perfused liquid at the outlet of the terminal orifice of said catheter.

4. Apparatus according to claim 3, wherein the sum of cross-sectional areas of the discharge holes provided on the periphery of the distal end of the catheter is greater than the cross-sectional area of the terminal orifice of the catheter in order to reduce the force of the jet discharged through the terminal orifice of said catheter.

5. Apparatus according to claim 1, wherein the guide rod of the catheter is disposed outside said catheter and secured to the inflatable bulb, and the distal end of the catheter is provided with a plurality of discharge holes on its periphery in order to prevent a jet effect of blood or of another perfused liquid at the outlet of the terminal orifice of said catheter.

6. Apparatus according to claim 1, wherein the guide rod of the catheter is engaged in the free end of the catheter distally of the inflatable bulb, and outside said catheter proximately of said bulb, and wherein, proximately of a point where said guide rod enters in the corresponding end of the catheter and distally of said bulb, said catheter is provided with holes for discharge of blood or of physiological liquid to be performed.

7. Apparatus according to claim 1, wherein the guide rod of the catheter has a cross-sectional area which is distinctly smaller than the internal space of said catheter in order to leave a free passageway for the liquid to be perfused and said guide rod can have a larger cross-section at the free end beyond the terminal orifice of the catheter while nevertheless being capable of sliding within said catheter.

8. Apparatus according to claim 1, wherein said guide rod is mounted on the catheter.

9. Apparatus according to claim 1, wherein said guide rod is mounted on the inflatable bulb carried by said catheter.

10. Apparatus for the performance of a long-duration angioplasty of a coronary artery or of a peripheral artery, comprising a catheter having a flexible guide rod and a dilation bulb which is located at a distal end of said catheter and is intended to be inflated at the required location, further comprising:

a perfusion pump connected at a proximate end of the catheter, and a control unit connected to said pump and which is capable of ensuring synchronization of the operation of said pump with the electrocardiogram of the patient to be treated in order to carry out distally of the dilation bulb a perfusion of blood or of oxygen-transporting physiological liquid at a variable flow rate and pressure corresponding to the physiological diastole and systole phases of the patient's heartbeat, wherein said guide rod extends along said catheter so as not to interfere with the circulation of liquid through the catheter and at the outlet of said catheter, and wherein said guide rod and said catheter are so dimensioned as to permit substantially free perfusion of blood through said catheter, in order to permit perfusion of blood or of physiological liquid distally of the dilation bulb throughout the period of inflation of said bulb;

and wherein the unit for controlling the perfusion pump comprising a number of separate control devices designed to produce operation of said pump in accordance with the particular characteristics of the flow curve, during the diastole and systole phases, which is characteristic of one of the arteries to be treated, a control element for putting one device or another into service according to requirements, and the arrangement of the control unit being such that the operation of the device which is put into service is made dependent on the patient's electrocardiogram, in regard to the moment of starting of the diastole and systole phases.

11. Apparatus according to claim 10 wherein the guide rod is positioned within the catheter and is adapted to be withdrawn from the catheter after positioning of the dilation bulb at the required location, and the distal end of said catheter is provided with a plurality of discharge holes on its periphery in order to prevent any jet effect of blood or of another perfused liquid at the outlet of the terminal orifice of said catheter.

12. Apparatus according to claim 11, wherein the sum of cross-sectional areas of the discharge holes provided on the periphery of the distal end of the catheter is greater than the cross-sectional area of the terminal orifice of the catheter in order to reduce the force of the jet discharged through the terminal orifice of said catheter.

13. Apparatus according to claim 10, wherein the guide rod of the catheter is disposed outside said catheter and secured to the inflatable bulb, and the distal end of the catheter is provided with a plurality of discharge holes on its periphery in order to prevent a jet effect of blood or of another perfused liquid at the outlet of the terminal orifice of said catheter.

14. Apparatus according to claim 10, wherein the guide rod of the catheter is engaged in the free end of the catheter distally of the inflatable bulb and outside said catheter proximately of said bulb, and wherein, proximately of a point where said guide rod enters in the corresponding end of the catheter and distally of said bulb, said catheter is provided with holes for discharge of blood or of physiological liquid to be performed.

15. Apparatus according to claim 10, wherein the guide rod of the catheter has a cross-sectional area which is distinctly smaller than the internal space of said catheter in order to leave a free passageway for the liquid to be perfused and said guide rod can have a larger cross-section at the free end beyond the terminal orifice of the catheter while nevertheless being capable of sliding within said catheter.

16. Apparatus according to claim 10, further comprising a tube extending into the inflatable bulb for inflating said bulb, said tube being secured to said catheter and having a substantially smaller diameter than said catheter.

17. Apparatus according to claim 10, wherein said guide rod is mounted on the catheter.

18. Apparatus according to claim 10, wherein said guide rod is mounted on the inflatable bulb carried by said catheter.

* * * * *